United States Patent
Xu et al.

(10) Patent No.: US 11,142,798 B2
(45) Date of Patent: Oct. 12, 2021

(54) SYSTEMS AND METHODS FOR MONITORING LIFELONG TUMOR EVOLUTION FIELD OF INVENTION

(71) Applicant: GenomiCare Biotechnology (Shanghai) Co. Ltd, Shanghai (CN)

(72) Inventors: Qiang Xu, Shanghai (CN); Guan Wang, Shanghai (CN); Chun Dai, Shanghai (CN)

(73) Assignee: GENOMICARE BIOTECHNOLOGY (SHANGHAI) CO. LTD, Shanghai (CN)

( * ) Notice: Subject to any disclaimer, the term of this patent is extended or adjusted under 35 U.S.C. 154(b) by 389 days.

(21) Appl. No.: 15/519,152

(22) PCT Filed: Nov. 17, 2016

(86) PCT No.: PCT/CN2016/106284
§ 371 (c)(1),
(2) Date: Sep. 5, 2018

(87) PCT Pub. No.: WO2018/090298
PCT Pub. Date: May 24, 2018

(65) Prior Publication Data
US 2019/0010552 A1    Jan. 10, 2019

(51) Int. Cl.
*C12Q 1/68* (2018.01)
*C12Q 1/6886* (2018.01)
*G16B 40/00* (2019.01)
*C12Q 1/6809* (2018.01)
*C12N 15/00* (2006.01)

(52) U.S. Cl.
CPC ........... *C12Q 1/6886* (2013.01); *C12N 15/00* (2013.01); *C12Q 1/6809* (2013.01); *G16B 40/00* (2019.02); *C12Q 2600/106* (2013.01); *C12Q 2600/156* (2013.01)

(58) Field of Classification Search
CPC ............... C12Q 1/6886; C12Q 1/6809; C12Q 2600/106; C12Q 2600/156; C12Q 2600/16; C12Q 2535/122; C12Q 2537/16; C12Q 2600/112; C12N 15/00; G06F 19/24; G16B 40/00
See application file for complete search history.

(56) References Cited

U.S. PATENT DOCUMENTS

2016/0032396 A1* 2/2016 Diehn ................... G16B 30/00 506/2
2018/0363066 A1* 12/2018 Chalmers ............. C12Q 1/6806
2019/0219586 A1* 7/2019 Fabrizio .................. A61P 35/04

* cited by examiner

*Primary Examiner* — David C Thomas
(74) *Attorney, Agent, or Firm* — Lin Sun-Hoffman; Yong Chen; Liu Chen & Hoffman LLP

(57) ABSTRACT

Disclosed are for monitoring tumor load in a patient by selecting a predetermined number of biomarker genes from DNA extracted from a tumor tissue sample from the patient to form a panel of biomarker genes ("customized genes"); isolating circulating cell-free DNA from a bodily fluid (body fluid) sample of the patient; enriching DNA sequences containing the biomarker genes in the cell-free DNA fragments; sequencing the enriched DNA; counting the number of mutated DNA and normal DNA sequencing reads in enriched DNA; and obtaining a tumor load of the patient. Optionally, the detection of mutations in genes related to therapeutic treatments ("medicine genes") are carried out simultaneously with the testing of customized genes.

20 Claims, 8 Drawing Sheets
Specification includes a Sequence Listing.

SYSTEMS AND METHODS FOR MONITORING LIFELONG TUMOR EVOLUTION FIELD OF INVENTION

FIELD OF INVENTION

The invention relates generally to the field of precision medicine, specifically systems and methods for monitoring tumor load in a patient by testing customized circulating tumor DNA in a blood sample from the patient, and optionally further in combination with the detection of mutations in genes related to therapeutic treatments.

BACKGROUND

Human cancer develops under Darwinian evolution where generic or epigenetic variation alters molecular phenotypes in individual cells. As tumors grow, mutations arise and populations of genetically distinct cells emerge. As a result, tumors at diagnosis often include multiple, genotypically distinct cell populations or clones, which are related through a phylogeny and act as substrates for selection in tumor microenvironments or with therapeutic intervention. The tumor cells which are able to adapt to new medications become resistant to treatment, survive and expand. It has been difficult to unpick this process, because cancer evolves inside the body over the course of years. It would require a comprehensive knowledge of tumor specific mutations and the adaptive process in order to piece together a more precise picture of how cancer evolves, reveal the roots of resistance and find out how it might be overcome.

Current technologies fail to capture a precise evolution of tumor mutations over the course of tumor development. For example, tissue biopsies are invasive and often limited spatially and timely due to limitations of tissue dissection. Current non-invasive methods of circulating tumor DNA sequencing fails to address the variation of tumor specific mutations in different patients and the cumbersome testing procedures. It is therefore desirable to develop new techniques to monitor the tumor cell mutations in a non-invasive, precise, and evolutionary manner.

BRIEF SUMMARY OF THE INVENTION

One aspect of the present invention is a method for monitoring tumor load in a patient. The method comprises the steps of (a) selecting a predetermined number of biomarker genes from DNA extracted from a tumor tissue sample from the patient to form a panel of biomarker genes ("customized genes"); (b) isolating circulating cell-free DNA from a bodily fluid (also known as body fluid) sample of the patient; (c) enriching DNA sequences containing the biomarker genes in the cell-free DNA fragments; (d) sequencing the enriched DNA; (e) counting the number of mutated DNA and normal DNA sequencing reads in enriched DNA; and (f) obtaining a tumor load of the patient.

In some embodiments, the panel of biomarker gene includes at least 5 biomarker genes. In other embodiments, the panel of biomarker genes includes 5-10 biomarker genes. In still other embodiments, the panel of biomarker genes includes 11-20 biomarker genes. In further embodiments, the panel of biomarker genes includes 21-30 biomarker genes. In some further embodiments, the panel of biomarker genes includes 31-50 biomarker genes.

In some embodiments, the enrichment step comprises the steps of performing a multiplex PCR with primers specific to the biomarker genes in the panel of biomarker genes; and adding adaptors to the amplified DNA to obtain a library.

In some embodiments, the sequencing step is performed on the Ion S5 NGS platform. In other embodiments, the method of monitoring tumor load further comprises the step of guiding a treatment option for the patient based on the obtained cell-free tumor load of the patient.

In further embodiments of the method for monitoring tumor load, the steps b-f are repeated in a periodic manner. In some instances, the steps of b-f is repeated once every 1-3 months.

In some embodiments, the method further comprises selecting a predetermined number of biomarker genes by (a) determining somatic mutations in the DNA extracted from the tumor tissue sample of the patient; (b) calculating a somatic mutation clonal ratio (CR) for each somatic mutation; (c) ranking the somatic mutation clonal ratios for all somatic mutations; and (d) selecting a predetermined number of somatic mutations as biomarker genes that are ranked among the highest.

In some embodiments, the step of calculating somatic mutation clonal ratio (CR) comprises (a) determining the percentage of tumor cell in the tumor tissue (TP); (b) determining, for each somatic mutation, somatic mutation allele ratio (SA); (c) determining, for each somatic mutation, an average of the scores or values of a predetermined number of true germline hyterozygosis SNPs in normal tissue nearest to the position of the somatic mutation (PLG); (d) determining, for each somatic mutation, copy number variation (CNVR); and (e) calculating the somatic mutation clonal ratio by $$CR = \frac{SA}{PLG - 0.5 \times \frac{1-TP}{CNVR}}.$$

In some embodiments, the step of obtaining a tumor load of the patient comprises (a) for each biomarker gene in the panel, obtaining a somatic mutation allele ratio in circulating tumor DNA test by (i) counting the number of total circulating DNA reads; (ii) counting the number of circulating DNA with the somatic mutation allele; and (iii) dividing the number of circulating DNA with the somatic mutation allele with the number of total circulating DNA reads to obtain the somatic mutation allele ratio; (b) for each biomarker gene in the panel, obtaining a somatic mutation clonal ratio as in claim 12; and (c) obtaining the tumor load based in an average of the ratio of each somatic mutation allele ratio over the corresponding somatic mutation clonal ratio.

In some embodiments, the step off determining the percentage of tumor cell in the tumor tissue (Tumor Purity) comprises (a) selecting true germline heterozygosis SNPs (THS) from the common SNPs in normal tissue; (b) detecting the THS in tumor tissue; (c) plotting a density vs. THS allele ratio; and (d) calculating the percentage of tumor cell in the tumor tissue based on the detected THS in the tumor tissue.

In some embodiments, the step of detecting THS in the tumor tissue comprises (a) calling each THS allele score in the tumor tissue; (b) using an algorithm to smooth score sets density curve; (c) identifying the positions of two minor shoulder peaks on the density vs. TH allele ratio of the tumor tissue; and (d) determining the percentage of tumor cell in the tumor tissue by TP=((100−(A+B))/2+A)/100, where A is the position of a first of the minor shoulder peaks identified, and the B is the position of a second of the minor shoulder peaks identified.

In some embodiments, the method of monitoring tumor load further comprises the detection of mutations in genes related to therapeutic treatments ("medicine genes"). In some embodiments, the detection of mutations in genes related to drug sensitivity comprises (a) enriching DNA sequences containing the medicine genes in the cell-free circulating DNA; (b) sequencing the enriched DNA; and (c) counting the number of mutated DNA and the number of enriched DNA sequences.

In some embodiments, the enriching, sequencing and counting steps in the detection of mutations in medicine genes are performed simultaneously with the enriching, sequencing and counting steps in obtaining the tumor load based on the customized genes. In some instances, the medicine genes are ERBB2, MET, EGFR, KRAS, PIK3CA, BRAF, KIT, NRAS, ALK, ROS1, and RET. In some instance, the mutations of the medicine genes may comprise single nucleotide changes, copy number variations, insertions, deletions, fusions, and inversions.

DETAILED DESCRIPTION OF THE INVENTION

The present disclosure is directed to new and novel systems and methods for monitoring tumor cell evolution by testing circulating tumor DNA. The systems and methods are partly based on our new discovery that clonal ratio of somatic mutations can be derived from exome sequencing of tumor tissues and tumor specific mutations can be selected to for a customized gene panel based on the ranking of the clonal ratios with the higher clonal ratio representing a more specific tumor mutation. When combined with the clonal ratios of somatic mutations, allele ratios in circulating DNA for each of the somatic mutations can be used to derive tumor loads in a patient and thereby to monitor the tumor mutations in a non-invasive, precise, and evolutionary manner.

In one aspect, the present disclosure is directed to a method for monitoring tumor load in a patient by selecting a predetermined number of biomarker genes from DNA extracted from a tumor tissue sample from the patient to form a panel of biomarker genes ("customized genes"); isolating circulating cell-free DNA from a bodily fluid sample of the patient; enriching DNA sequences containing the biomarker genes in the cell-free DNA fragments; sequencing the enriched DNA; counting the number of mutated DNA and normal DNA in enriched DNA; and obtaining a tumor load of the patient. In some instances, the bodily fluid is a blood, blood serum, amniotic fluid, spinal fluid, conjunctival fluid, salivary fluid, vaginal fluid, stool, seminal fluid, urine or sweat.

Figure 1:
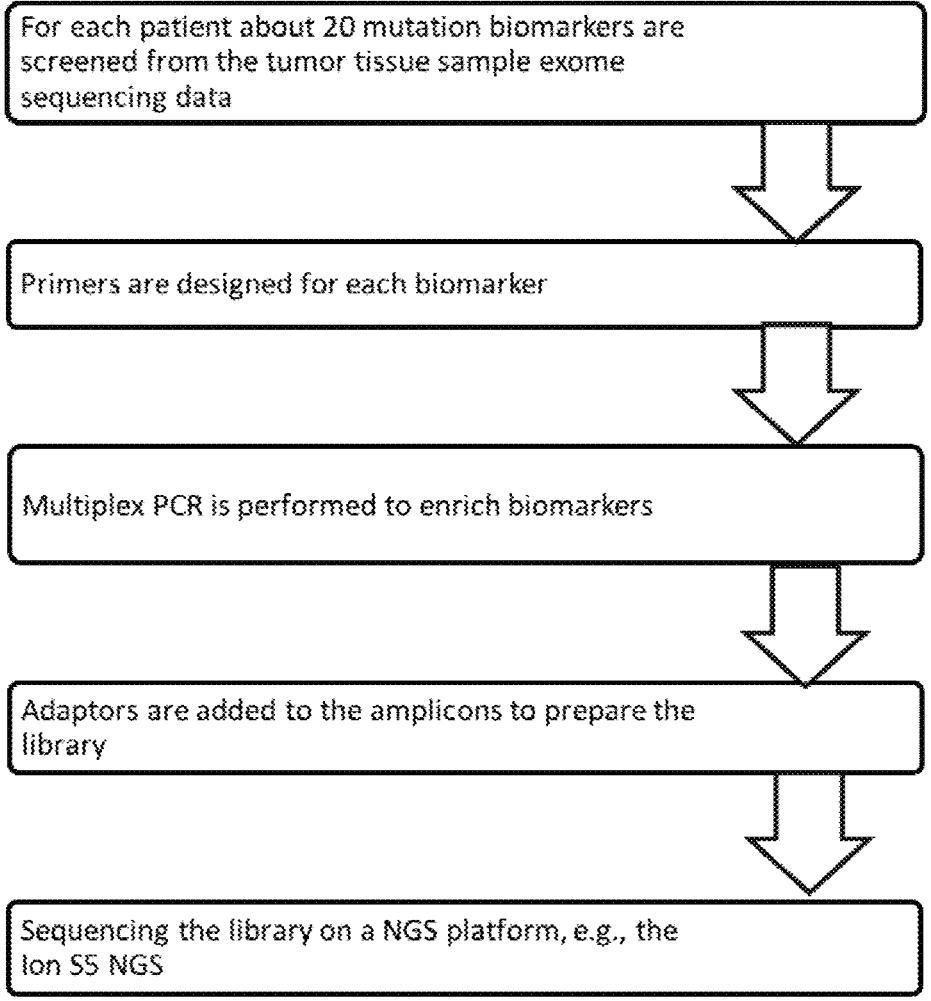
FIG. 1 shows a flow chart depicting the process for monitoring tumor evolution.

In one example, as shown in the flow chart in FIG. 1, a customized gene or biomarker gene panel including 20 mutation biomarkers are selected based on exome sequencing data of tissue samples; primers are then designed for each biomarker; the biomarkers are enriched through multiplex PCR with the primers; adapters are added to the amplicons to prepare sequencing library and finally the prepared library is subject to sequencing on a next generation sequencing platform.

In some embodiments, the tissue samples may be sample of formalin-fixed paraffin-embedded (FFPE) tissue, fresh frozen (FF) tissue, or tissue comprised in a solution that preserves nucleic acid or protein molecules. A sample can be without limitation fresh, frozen or fixed. Samples can be associated with relevant information such as age, gender, and clinical symptoms present in the subject; source of the sample; and methods of collection and storage of the sample. A sample is typically obtained from a subject.

In other embodiments, a tissue sample is a sample derived from a biopsy. The biopsy may comprise the process of removing a tissue sample for diagnostic or prognostic evaluation, and to the tissue specimen itself. Any biopsy technique known in the art can be applied to the methods of the present invention. The biopsy technique applied can depend on the tissue type to be evaluated (e.g., colon, prostate, kidney, bladder, lymph node, liver, bone marrow, blood cell, lung, breast, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. Molecular profiling can use a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

In a method of enriching Standard molecular biology techniques known in the art and not specifically described are generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons. Baltimore, Md. (1989) and as in Perbal, A Practical Guide to Molecular Cloning, John Wiley & Sons, New York (1988), and as in Watson et al., Recombinant DNA. Scientific American Books, New York and in Birren et al (eds) Genome Analysis: A Laboratory Manual Series. Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) can be carried out generally as in PCR Protocols: A Guide to Methods and Applications, Academic Press, San Diego, Calif. (1990).

In one embodiment, the selection of the predetermined number of biomarker genes is to select tumor specific mutations. In some instances, the tumor specific mutations are selected according to how often the mutation is represented in tumor cells. The higher percentage of tumor cells having a mutation, the more specific a mutation is to the tumor. The percentage of tumor cells having a mutation among all tumor cells is hereby called the clonal ratio of the tumor mutation. The higher the clonal ratio, the more specific the tumor mutation is to the tumor. For example, in one method, somatic mutations in the DNA extracted from the tumor tissue sample of the patient are first identified; a somatic mutation clonal ratio (CR) for each somatic mutation is then calculated; the somatic mutation clonal ratios for all somatic mutations are ranked from high to low; and those somatic mutations that are ranked among the highest are selected to form a panel of somatic mutations as biomarker genes. This panel of biomarker genes are also referred to customized genes in the disclosure.

Figure 3:
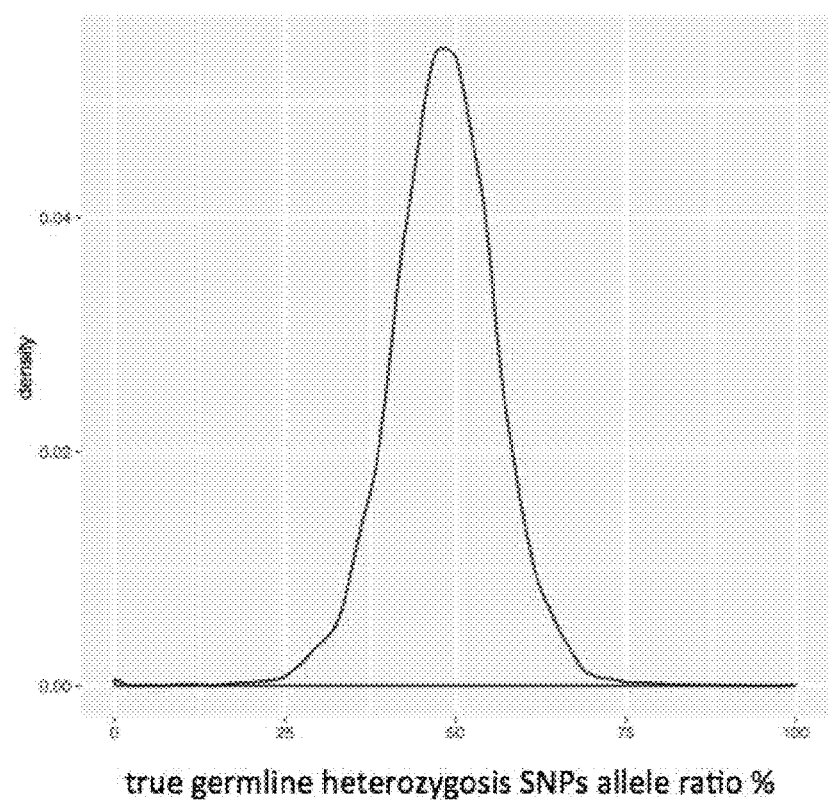
FIG. 3 shows a graph depicting the true germline heterozygosis SNPs allele ratio being 50%.

The percentage of tumor cell in the tumor tissue (Tumor Purity, or TP) may be determined through the analysis of true germline heterozygosis SNPs. In one example, TP may be obtained by selecting true germline heterozygosis SNPs (THS) from the common SNPs in normal tissue; detecting THS in the tumor tissue; plotting a density vs. THS allele ratio; and calculating the percentage of tumor cell in the tumor tissue based on the detected THS in the tumor tissue. As shown in FIG. 3, for true germline heterozygosis SNPs, the density peak is around 50%.

Figure 4:
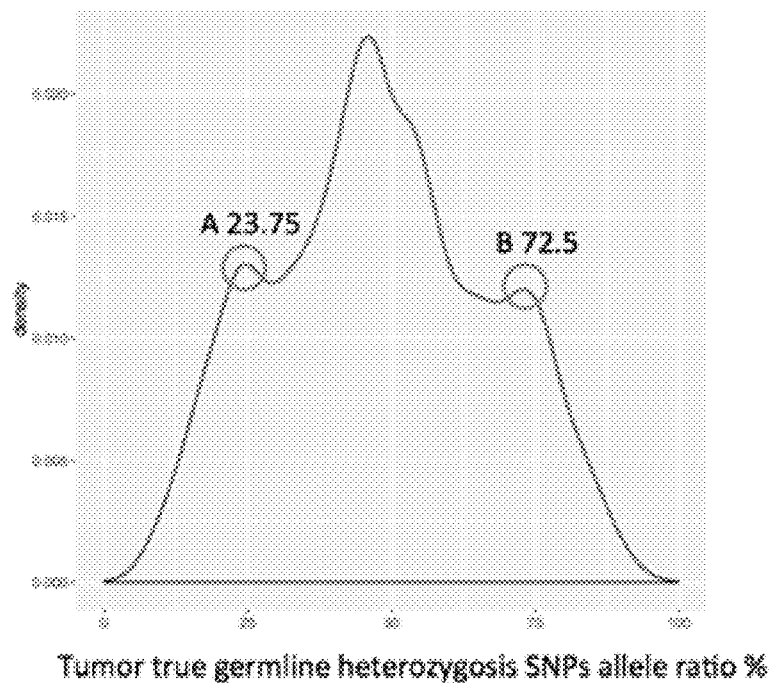
FIG. 4 shows a graph depicting the tumor true germline heterozygosis SNPs allele ratios being 72.5% and 23.75%.

In some embodiments, the detection of THS in the tumor tissue comprises the steps of (i) calling each THS allele score in the tumor tissue; (ii) using an algorithm to smooth score sets density curve; (iii) identifying the positions of two minor shoulder peaks on the density vs. TH allele ratio of the tumor tissue; and (iv) determining the percentage of tumor cell in the tumor tissue by TP=((100−(A+B))/2+A)/100, where A is the position of a first of the minor shoulder peaks identified, and the B is the position of a second of the minor shoulder peaks identified. An example is shown in FIG. 4, wherein the density of tumor true germline heterozygosis allele diversifies in to 23.75% and 72.5%. Based on the diversification, the TP is calculated to be 25.652%.

In some embodiment, the calculation of somatic mutation clonal ratio (CR) comprises the following steps: (i) determining the percentage of tumor cell in the tumor tissue (Tumor Purity, or TP); (ii) determining, for each somatic mutation, somatic mutation allele ratio (SA); (iii) determining, for each somatic mutation, an average of the scores or values of a predetermined number of true germline hyterozygosis SNPs in normal tissue nearest to the position of the somatic mutation (PLG); (iv) determining, for each somatic mutation, copy number variation (CNVR); and (v) calculating the somatic mutation clonal ratio by $$CR = \frac{SA}{PLG - 0.5 \times \frac{1-TP}{CNVR}}.$$

Figure 5:
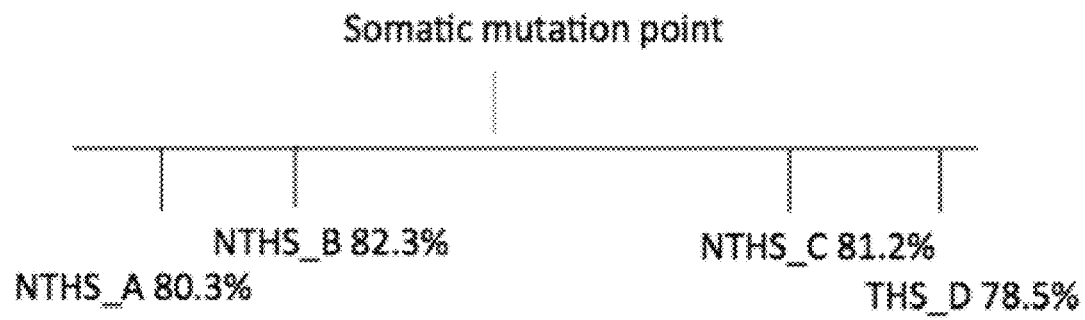
FIG. 5 shows a graph depicting SNP allele ratios that are linked to a somatic mutation point.

In some embodiments, for example as shown in FIG. 5, PLG is derived from an average of the scores or values of four true germline hyterozygosis SNPs in normal tissue nearest to the position of the somatic mutation (PLG= (80.3%+82.3%+81.2%+78.5%)/4=80.56%).

FIGS. 6A, 6B, 6C, 6D, and 6E illustrate some hypothetical exemplary scenarios showing how clonal ratios can be derived from exome sequencing data. The red bar refers to somatic mutation allele (labeled with SA). The blue bars (labeled with NTHS) refers to nearest true heterozygosis SNPs.

Figure 6A:
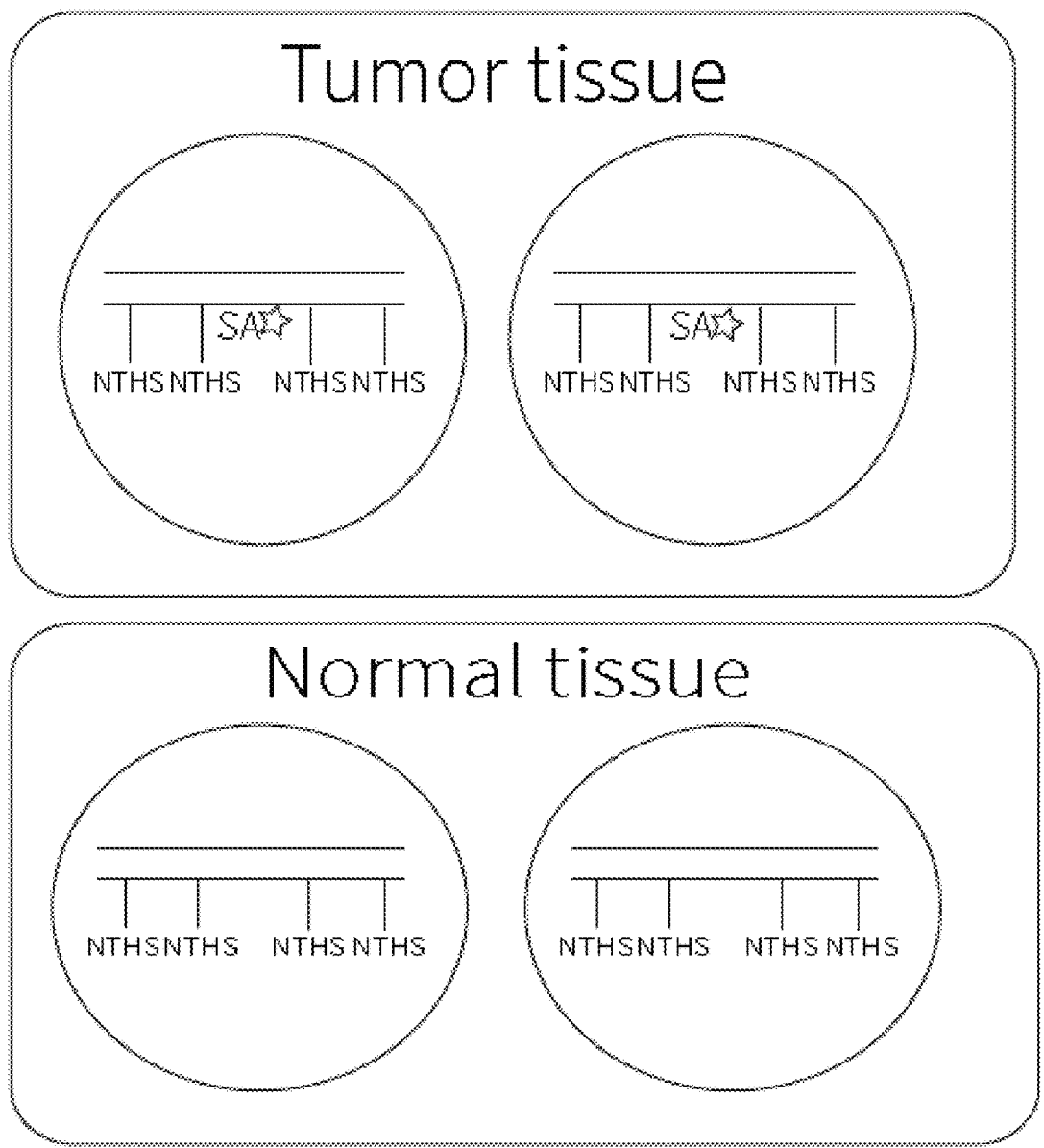
FIGS. 6A, 6B, 6C, 6D, and 6E illustrates the derivation of somatic mutation clonal ratios (CR) in different scenarios. TP: tumor purity; SA, somatic mutation allele ratio: PLG, the average of four nearest true germline heterozygosis SNPs; CNVR: copy number variation.

In scenario 1 shown in FIG. 6A tumor purity (TP) is 100%, meaning in the tissue all cells are tumor cells; somatic allele ratio (SA) is 50%, meaning 50% of the alleles are mutant from the tumor cells; PLG is 50%; and CNVR is 1, meaning there is no copy number variation. In Scenario 1, according to the CR calculation formula, the somatic mutation clonal ratio (CR) is therefore 100%, suggesting that all tumor cells have the somatic mutation.

Figure 6B:
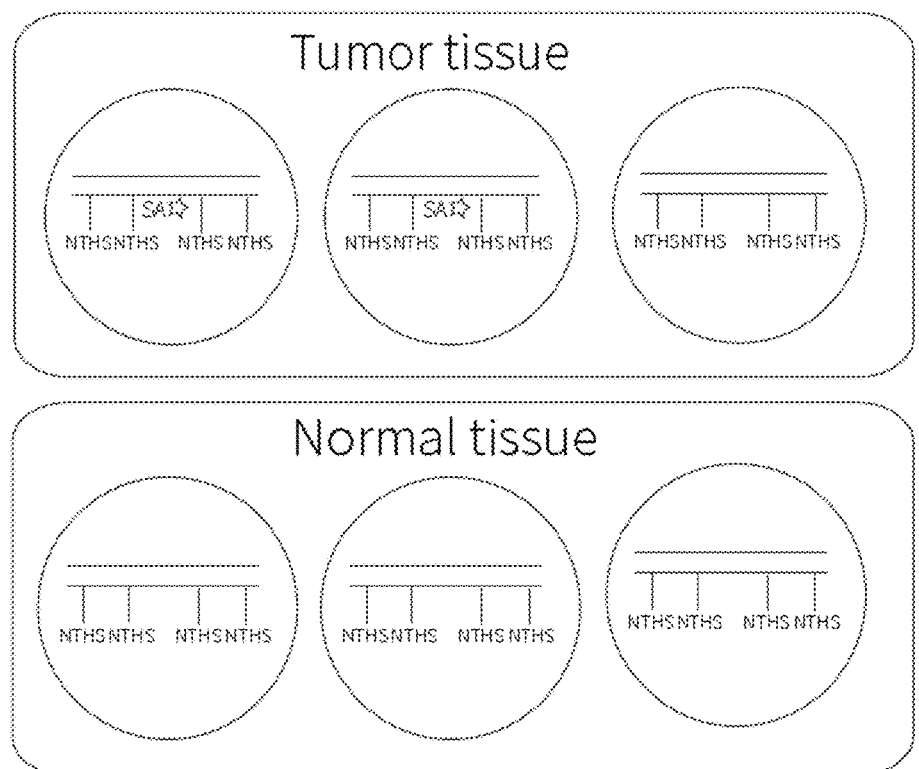

In scenario 2 shown in FIG. 6B, TP is 2/3, meaning 2/3 of the tumor tissue cells are actual tumor cells; SA is 1/3, meaning 1/3 of the alleles are mutant in the tumor tissue cells; PLG is 50%; CNVR is 1. In Scenario 2, CR will be 100%, suggesting all tumor cells have the somatic mutation.

Figure 6C:
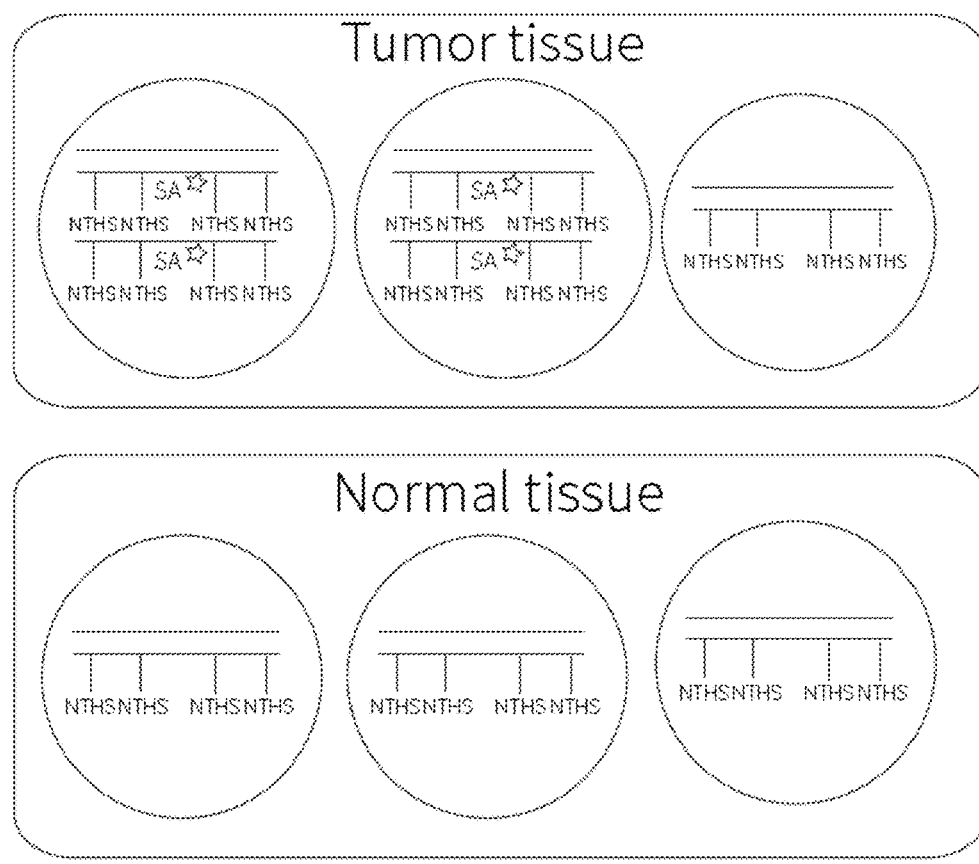

In scenario 3 shown in FIG. 6C, TP is 2/3, meaning 2/3 of the tumor tissue cells are actual tumor cells; SA is 4/8, meaning 4/8 of the alleles are mutant in the tumor tissue cells; PLG is 5/8; CNVR is 8/6, meaning there are two chromosome duplications. In Scenario 3, CR will be 100%, suggesting all tumor cells have the somatic mutation.

Figure 6D:
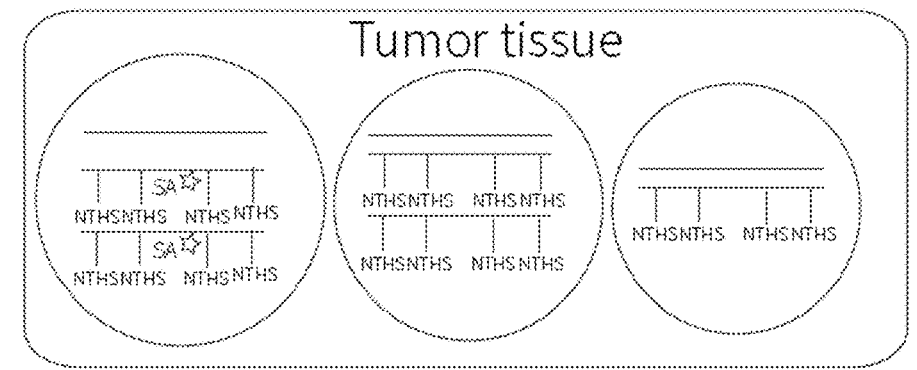
Figure 6D:
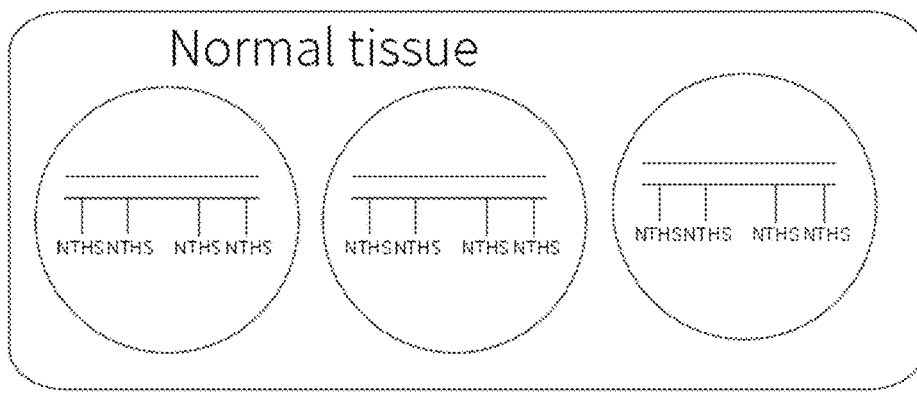

In scenario 4 shown in FIG. 6D, TP is 2/3, meaning 2/3 of the tumor tissue cells are actual tumor cells; SA is 2/8, meaning 2/8 of the alleles are mutant in the tumor tissue cells; PLG is 5/8; CNVR is 8/6, meaning there are two chromosome duplications. In Scenario 4, CR will be 50%, suggesting 50% tumor cells have the somatic mutation.

Figure 6E:
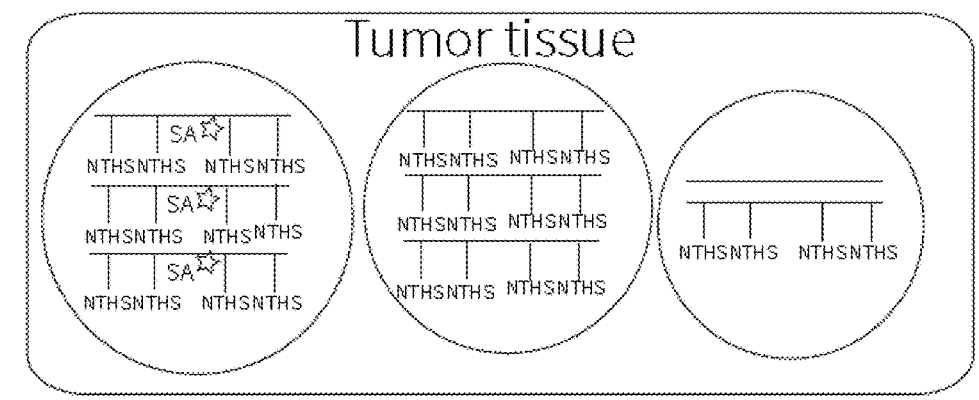
Figure 6E:
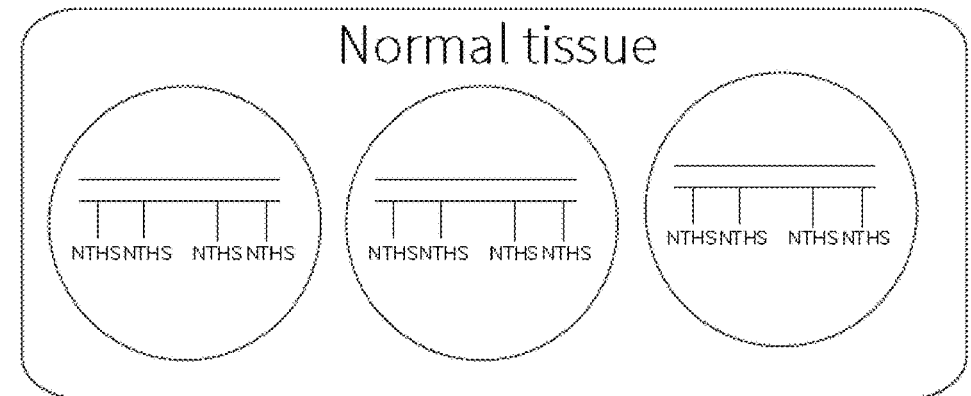

In scenario 5 shown in FIG. 6E, TP is 2/3, meaning 2/3 of the tumor tissue cells are actual tumor cells; SA is 3/8, meaning 3/8 of the alleles are mutant in the tumor tissue cells; PLG is 7/8; CNVR is 8/6, meaning there are two chromosome duplications. In Scenario 5, CR will be 50%, suggesting 50% tumor cells have the somatic mutation.

With the clonal ratio is obtained through exome sequencing of tumor tissue samples, the tumor load of the patient may be derived by fin for, obtaining a somatic mutation allele ratio in circulating tumor DNA for each biomarker gene in the panel by (i) counting the number of total circulating DNA reads; (ii) counting the number of circulating DNA with the somatic mutation allele; and (iii) dividing the number of circulating DNA with the somatic mutation allele with the number of total circulating DNA reads to obtain the somatic mutation allele ratio; and then obtain the tumor load based in an average of the ratio of each somatic mutation allele ratio over the corresponding somatic mutation clonal ratio.

The number of biomarker genes selected based on clonal ratios may vary. In some embodiments, the customized gene panel includes at least 5 biomarker genes. In other embodiments, the panel of biomarker genes may include 5-10 biomarker genes. In still other embodiments, the panel of biomarker genes may include 11-20 biomarker genes. In further embodiments, the panel of biomarker genes may include 21-30 biomarker genes. In still further embodiments, the panel of biomarker genes may include more than 30 biomarkers genes.

In some embodiments, a sample is taken from a patient periodically over the course of tumor development. Tumor load is then derived by examining circulating tumor DNAs according to the above methods. In some instances, samples are taken every 1-3 months. On other instances, samples are taken every 1-3 weeks when necessary.

In some embodiments, the method of monitoring tumor load with tumor specific mutations is carried out simultaneously with testing mutations in genes that are related to therapeutic treatments. These genes are hereby referred to as medicine genes. Any genes that are now known or future found to be associated with therapeutic treatments of cancer or tumors can be included in the medicine gene panel.

In one exemplary instance, the testing of the medicine genes comprises the steps of enriching DNA sequences containing the medicine genes in the cell-free circulating DNA; sequencing the enriched DNA; and counting the number of mutated DNA and the number of enriched DNA sequences. In some embodiments, primers are designed for these medicine genes and used to enrich the medicine genes in amplication reactions. These amplication reactions for the medicine genes may be carried separately from the amplification reactions fro the customized genes. In some embodiments, the two amplification producted may be combined at the sequencing and counting steps, thereby simplifying the procedures to test both the customized and medicine genes.

In some embodiments, the medicine genes are ERBB2, MET, EGFR, KRAS, PIK3CA, BRAF, KIT, NRAS, ALK, ROS1, and RET, that are related to therapeutic treatments. For example, the presence of mutation of KRAS, G13D suggest that the tumor is Panitumumab tolerant. The presence of mutation of PIK3CA E545K suggest that the tumor is Everolimus sensitive. More information is presented in Table 3 below.

In some embodiments, the mutations of the medicine genes and customized genes comprises single nucleotide changes, copy number variations, insertions, deletions, fusions, and inversions.

Figure 2:
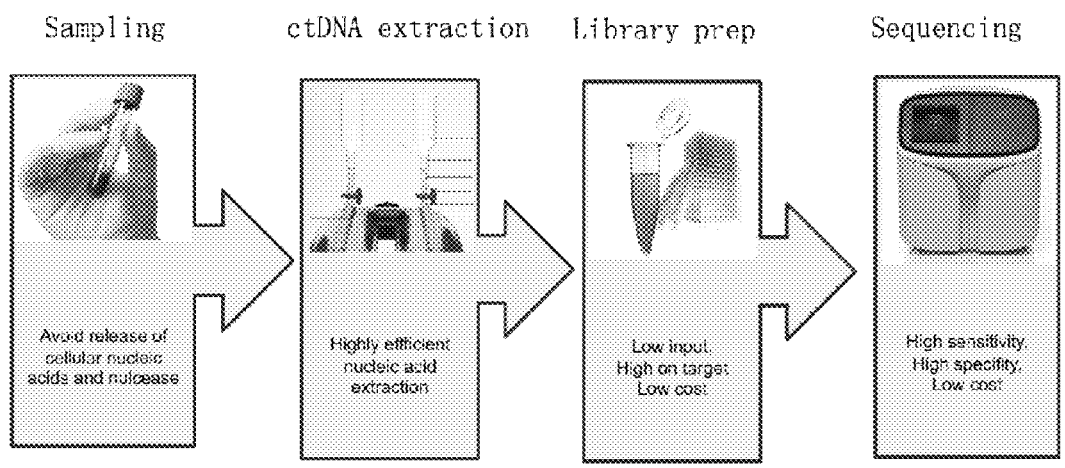
FIG. 2 shows a flow chart depicting the streamlined procedure for circulating tumor DNA analysis.

In another aspect, the present invention is directed to a streamlined process for circulating tumor DNA analysis. In one exemplary example of the streamlined process for circulating tumor DNA analysis, as shown in FIG. 2, sampling can be carried out by collecting plasma samples in a Strcl cell-free DNA tube, which is then subject to high efficient and cost-optimized extraction of nucleic acid. The exacted nucleic acid is then used to generate an individualized library of about 20 biomarkers, which library is used for subsequent sequencing on an Ion S5 NGS platform.

As used in this application, including the appended claims, the term "about," particularly in reference to a given quantity, is meant to encompass deviations of plus or minus ten percent.

As used herein, the singular forms "a," "an," and "the" include plural references, unless the content clearly dictates otherwise, and are used interchangeably with "at least one" and "one or more."

As used herein, the terms "comprises," "comprising." "includes." "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

Examples

1. Use of Circulating Tumor DNA in Monitoring Tumor Load.

The example describes the use of the circulating tumor DNA to monitor tumor load in a human subject. Specifically, a patient who was a 55-year-old female with metastatic colon cancer took 3 ctDNA tests. She received colectomy in February 2015. Pathology review confirmed Stage IV metastatic synchronous adenocarcinoma (pT4N2M1) and WES showed KRAS wild-type and no BRAF V600E mutation. The patient received chemotherapy each 3-week cycle×3 with capecitabine/oxaliplatin plus bevacizumab after surgical treatment since March 2015. The regimen remained on maintenance capecitabine and bevacizumab for 9 months before progression in liver metastases. Then transarterial chemoembolization (TACE) was performed with oxaliplatin.

Exome sequencing was performed with formalin-fixed, paraffin-embedded (FFPE) tissue, the tumor sample and the matched normal blood sample from the patient. DNA was extracted through the Maxwell® RSC Instrument, an automated DNA extraction system from Promega, according to the manufacturer's instructions. Maxwell RSC DNA FFPE Kit and Maxwell RSC Whole Blood DNA Kit (Promega) were used for DNA isolation from FFPE tissue and normal peripheral blood leucocytes respectively. The pure high molecular weight genomic DNA samples were quality-checked on agarose gels and quantified using Qubit 3.0 (Thermo fishers)

DNA samples were sheared using Covaris S220. Libraries were prepared using the Agilent SureSelect Human All Exon v5 kit (Agilent Technologies), according to the manufacturer's instructions. DNA fragments of 200 bp in size were sequenced using paired-end 150 bp reads on HiSeqX (illumina) achieving mean depth of $>=200\times$ for tumor DNA and $>=100\times$ for normal DNA.

Then, each read was aligned to hg19 (February 2009 GRCh37/hg19) from UCSC Genome Browser using BWA (Burrows-Wheeler Aligner) with default parameters. The germline and somatic mutations were called using GATK (The Genome Analysis Toolkit 1.6) standard packages. Common dbSNPs (dbSNP 142 database) in LOH regions are easy to estimate the tumor purity in tumor tissue. After getting the tumor cell percentage in tumor tissue, we can directly calculate the mutated clonal ratio (all tumor cells divided by mutated tumor cells) for each somatic mutation point. So we can select top 30 the somatic mutation points based on the clonal ratio rank from high to low and 23 of 30 somatic mutation sites have successfully been designed PCR primers.

As shown in Table 1, 23 somatic tumor mutation biomarkers were selected. Primers were designed for each of the 23 mutation biomarkers but 17 mutation biomarkers were in the final panel with a design rate of 74%. The primers were designed through online tools of Ion AmpliSeq Designer (https://ampliseq.com). According to the website's wizard, a file in CSV format indicated the genomic coordinate of each mutation was uploaded. Application type was DNA hotspot designs. Reference genome was Human (hg19). After several hours processing, the design's result was ready and the primers sequences listed in Table 2.

TABLE 1

Somatic Tumor Mutations Identified in Exome Sequencing.

| GeneName | Type | Chromosom | Position | Reference | Altration | Frequency % (FFPE exome) |
|---|---|---|---|---|---|---|
| CHD5 | sequence_feature | 1 | 6196771 | C | T | 41.7 |
| KIF17 | missense_variant | 1 | 21036291 | C | T | 35.3 |
| APC | stop_gained | 5 | 112175198 | C | T | 40.3 |
| FGF18 | missense_variant | 5 | 170863239 | G | A | 26.4 |
| CDH18 | missense_variant | 5 | 19721557 | A | T | 25 |
| TPP1 | splice_acceptor_variant&intron_variant | 11 | 6638091 | C | A | 41.8 |
| UQCRC2 | missense_variant | 16 | 21974100 | C | G | 63 |
| TP53 | stop_gained | 17 | 7577058 | C | A | 54.5 |
| FLT4 | synonymous_variant | 5 | 180057043 | G | A | 43.8 |
| VWDE | missense_variant | 7 | 12409586 | G | T | 34.6 |
| DUSP13 | missense_variant | 10 | 76867899 | T | C | 56.5 |
| SESN3 | missense_variant | 11 | 94906470 | C | T | 34.7 |
| BMP4 | synonymous_variant | 14 | 54418878 | C | T | 61.7 |
| SLC35G3 | missense_variant | 17 | 33521058 | C | T | 34.7 |
| CASKIN2 | sequence_feature | 17 | 73497828 | G | C | 25.6 |
| VWCE | missense_variant | 11 | 61048599 | C | A | 10 |
| BACE1 | sequence_feature | 11 | 117170531 | C | A | 10 |

Multiplex PCR was performed to enrich target biomarkers according to the following procedure. First, DNA was quantified by Qubit dsDNA HS assay kit using Qubit 3.0 fluorometer. Then amplification reaction was prepared as follows. (Y=10/C, C is the concentration of each ctDNA sample (ng/ul)). In our example, the concentrations of the three ctDNA samples are 0.178 ng/μl, 0.283 ng/μl, and 0.334 ng/μl, respectively. Accordingly, all the three Y values are more than 50 ul, so all the rest reaction volume were occupied with ctDNAs. i.e. Y=13 and no nuclease-free water added.

| Reagent | CtDNA sample |
|---|---|
| 2x Phusion HF PCR Master Mix | 25 |
| Taq Polymerase | 1 |
| DMSO | 1 |
| Customerized primers Mix(1 uM) | 10 |
| gDNA, 10 ng | Y ul |
| Nuclease-free Water | 13-Y ul |
| Total | 50 ul |

TABLE 2

Primers for the custom gene markers.

| Primer name | Sequence (from 5' to 3') |
|---|---|
| S1-TP53-F (SEQ ID NO: 1) | TAAAAGTGAATCTGAGGCATAACTGCA |
| S1-TP53-R (SEQ ID NO: 2) | CGCACAGAGGAAGAGAATCTCC |
| S1-APC-F (SEQ ID NO: 3) | AGTTCATTATCATCTTGTCATCAGCTGA |
| SI-APC-R (SEQ ID NO: 4) | TCACAGGATCTTCAGCTGACCTA |
| S1-FLT4-F (SEQ ID NO: 5) | GGTCTCGCACTGCAGGTAC |
| S1-FLT4-R (SEQ ID NO: 6) | CAATGATGGTGGCCTTGTCC |
| S1-BMP4-F (SEQ ID NO: 7) | CCCTGAATCTCGGCGACTTTTT |
| S1-BMP4-R (SEQ ID NO: 8) | CCCAGAGACACCATGATTCCTG |
| S1-FGF18-F (SEQ ID NO: 9) | CTACAGCCGGACCAGTGGGAAA |
| S1-FGF18-R (SEQ ID NO: 10) | GAAGGACATGTACACGGGTACA |
| S1-UQCRC2-F (SEQ ID NO: 11) | CTCAAATGTTGGCTTTACATTTTTGACTC |
| S1-UQCRC2-R (SEQ ID NO: 12) | TGAGGCTGAAGGTCAGCTACTT |
| S1-TPP1-F (SEQ ID NO: 13) | CGAAGAGGCGCATGAACTGA |
| S1-TPP1-R (SEQ ID NO: 14) | CCCACAGTGTCCTCAATTCCTTAC |
| S1-VWCE-F (SEQ ID NO: 15) | GGAGGATGTGGGTAGTCGTG |
| S1-VWCE-R (SEQ ID NO: 16) | AGATGCTTCTGTTGCTTCCTGAG |
| S1-CHD5-F (SEQ ID NO: 17) | ATCAATCTTGTAGCTGTTTAAGACCCTAAAA |

TABLE 2-continued

Primers for the custom gene markers.

| Primer name | Sequence (from 5' to 3') |
|---|---|
| S1-CHD5-R (SEQ ID NO: 18) | AAGAACAACCAGTCCAAGGTAGG |
| S1-KIF17-F (SEQ ID NO: 19) | GTTCATCAGCGTGTAGCCGA |
| S1-KIF17-R (SEQ ID NO: 20) | CTCAGCTGAAGGAGCACCCAGA |
| S1-CDH18-F (SEQ ID NO: 21) | GCTGTTTCCATAGGTAGGGTCAT |
| S1-CDH18-R (SEQ ID NO: 22) | CAGCATACCCATTTTCTGTGTTCAAATTAA |
| S1-VWDE-F (SEQ ID NO: 23) | TGACAGAGGGTCAAGGTGCTAT |
| S1-VWDE-R (SEQ ID NO: 24) | CAGCCAAACGGATCTGGAAGAA |
| S1-DUSP13-F (SEQ ID NO: 25) | TGCTGCCGTAGAAGTCAGG |
| S1-DUSP13-R (SEQ ID NO: 26) | GGCATCAAGTGCCCTTCCT |

A separate amplification reaction was performed for the medicine related pool. In the medicine related pool, there are 11 gene mutations related to treatment regimes as shown in Table 3 below. The piers used were listed at Table 4.

TABLE 3

Medicine Pool genes.

| GENE | Variants | CFDA approved Drugs | Indications for CFDA approved Drugs |
|---|---|---|---|
| BRAF | G464E, G466V, G469A, V600E, etc. | Sorafenib | Hepatocellular carcinoma/Renal cell carcinoma |
| EGFR | G719A, T790M, L858R, L861Q, exon 19 del, etc. | activating mutation except T790M: Erlotinib/Gefitinib/Icotinib; T790M mutation: Resistance to Erlotinib/Gefitinib/Icotinib | Non-small cell lung carcinoma |
| ERBB2 | amplification, G776YVMA ins, etc. | Trastuzumab/Lapatinib | Breast carcinoma |
| KIT | A502_Y503dup, exon 11 del, D816V, etc. | Sorafenib/Sunitinib/Imatinib/Axitinib/ Everolimus | Hepatocellatar carcinoma/Renal cell carcinoma/Gastrointestinal stromal tumor, etc, |
| KRAS | G12D, G13D, Q61H, etc. | Wild Type: Cetuximab; Mutant Type: Resistance to Cetuximab | Colorectal carcinoma |
| MET | amplification, exon 14 skipping, Y1253D, etc. | Crizotinib | Non-small cell lung carcinoma |
| NRAS | G12D, G13D, Q61H, etc. | Wild Type: Cetuximab; Mutant Type: Resistance to Cetuximab | Colorectal carcinoma |
| PIX3CA | E542K, E545K, H1047R, etc. | Everolimus | Renal cell carcinoma/Gastrointestinal neuroendocrine carcinoma/Breast carcinoma, etc. |
| ALK | EML4-ALK fusion, NPM-ALK fusion, etc. | Crizotinib | Non-small cell lung carcinoma |
| RET | KIF5B-RET fusion, CCDC6-RET fusion, etc. | Sorafenib/Sunitinib | Hepatocellular carcinoma/Renal cell carcinoma/Gastrointestinal stromal tumor |
| ROS1 | FIG-ROS1 fusion, LC34A2-ROS1 fusion, etc. | Crizotinib | Non-small cell lung carcinoma |

TABLE 4

Primers for the Medicine Pool.

| Primer name | Sequence (from 5' to 3') |
|---|---|
| KRAS_1_F (SEQ ID NO: 27) | CATGTACTGGTCCCTCATTGCA |
| EGFR_1_F (SEQ ID NO: 28) | CAGGAACGTACTGGTGAAAACAC |

TABLE 4-continued

Primers for the Medicine Pool.

| Primer name | Sequence (from 5' to 3') |
|---|---|
| ERBB2_1_F (SEQ ID NO: 29) | GCCAGGGTATCTGGCTACA |
| BRAF_1_F (SEQ ID NO: 30) | TCAGTGGAAAAATAGCCTCAATTCTTACC |
| EGFR_2_F (SEQ ID NO: 31) | GAAGCCTACGTGATGGCCA |
| NRAS_1_F (SEQ ID NO: 32) | GTGGGATCATATTCATCTACAAAGTGGT |
| EGFR_3_F (SEQ ID NO: 33) | GCCTCTTACACCCAGTGGAGAA |
| KIT_1_F (SEQ ID NO: 34) | GGCACCGTTGAATGTAAGGCTTA |
| KIT_2_F (SEQ ID NO: 35) | CCCACAGAAACCCATGTATGAAGT |
| ERBB2_2_F (SEQ ID NO: 36) | CTCCCATACCCTCTCAGCGTA |
| PIK3CA_1_F (SEQ ID NO: 37) | AATCTTTTGATGACATTGCATACATTCGAA |
| EGFR_4_F (SEQ ID NO: 38) | GCCAGTTAACGTCTTCCTTCTCT |
| PIK3CA_2_F (SEQ ID NO: 39) | TACAGAGTAACAGACTAGCTAGAGACAATG |
| ERBB2_3_F (SEQ ID NO: 40) | GTGTGCACCGGCACAGACAT |
| KRAS_2_F (SEQ ID NO: 41) | TACCTCTATTGTTGGATCATATTCGTCCA |
| MET_1_F (SEQ ID NO: 42) | CAGTCAAGGTTGCTGATTTTGGT |
| BRAF_2_F (SEQ ID NO: 43) | TATTATGACTTCTCACAATCTCACCACAT |
| NRAS_2_F (SEQ ID NO: 44) | GACCTTAATATCCGCAAATGACTTGC |
| MET_2_F (SEQ ID NO: 45) | CTCTGTTTTAAGATCTGGGCAGTGAA |
| MET_3_F (SEQ ID NO: 46) | ACATTTCCAGTCCTGCAGTCAA |
| KIT_3_F (SEQ ID NO: 47) | TATTCACAGAGACTTGGCAGCCAGAA |
| KRAS_1_R (SEQ ID NO: 48) | GTAATAATCCAGACTGTGTTTCTCCCTT |
| EGFR_1_R (SEQ ID NO: 49) | GAAAATGCTGGCTGACCTAAAGC |
| ERBB2_1_R (SEQ ID NO: 50) | ACTTCTCACACCGCTGTGTT |
| BRAF_1_R (SEQ ID NO: 51) | CTTCATGAAGACCTCACAGTAAAAATAGGT |
| EGFR_2_R (SEQ ID NO: 52) | TTGTCTTTGTGTTCCCGGACAT |
| NRAS_1_R (SEQ ID NO: 53) | GATTACTGGTTTCCAACAGGTTCTTG |
| EGFR_3_R (SEQ ID NO: 54) | TGTGCCAGGGACCTTACCTTATA |
| KIT_1_R (SEQ ID NO: 55) | ACTGATATGGTAGACAGAGCCTAAACAT |
| KIT_2_R (SEQ ID NO: 56) | ACTGACCAAAACTCAGCCTGTT |
| ERBB2_2_R (SEQ ID NO: 57) | AGCCATAGGGCATAAGCTGTG |
| PIK3CA_1_R (SEQ ID NO: 58) | GTGGAAGATCCAATCCATTTTGTTGTC |
| EGFR_4_R (SEQ ID NO: 59) | AACTCACATCGAGGATTTCCTTGTT |
| PIK3CA_2_R (SEQ ID NO: 60) | TAGCACTTACCTGTGACTCCATAGAAA |
| ERBB2_3_R (SEQ ID NO: 61) | GTGGGCAGGTAGGTGAGTTC |
| KRAS_2_R (SEQ ID NO: 62) | TATTATAAGGCCTGCTGAAAATGACTGAAT |
| MET_1_R (SEQ ID NO: 63) | CTTGGTGGTAAACTTTTGAGTTTGCA |
| BRAF_2_R (SEQ ID NO: 64) | GACTCGAGTGATGATTGGGAGATTC |

TABLE 4-continued

Primers for the Medicine Pool.

| Primer name | Sequence (from 5' to 3') |
|---|---|
| NRAS_2_R (SEQ ID NO: 65) | AAACCTGTTTGTTGGACATACTGGA |
| MET_2_R (SEQ ID NO: 66) | GCTCGGTAGTCTACAGATTCATTTGAAAC |
| MET_3_R (SEQ ID NO: 67) | CTTGTAGATTGCAGGCAGACAGAT |
| KIT_3_R (SEQ ID NO: 68) | GCAGAGAATGGGTACTCACGTTTC |

For the medicine pool, the reaction mixture was made as follows.

| Reagent | CtDNA sample |
|---|---|
| 2x Phusion HF PCR Master Mix | 25 |
| Taq Polymerase | 1 |
| DMSO | 1 |
| medicine related primers Mix(1 uM) | 10 |
| gDNA, 10 ng | Y ul |
| Nuclease-free Water | 13-Y ul |
| Total | 50 ul |

The two PCR reactions were performed according to the following program.

| Stage | Temperature | time |
|---|---|---|
| Hold | 98° C. | 2 min |
| Cycle(5 cycles) | 98° C. | 15 sec |
|  | 65° C.(−1° C./cycle) | 50 sec |
| Cycle(20 cycles) | 98° C. | 15 sec |
|  | 60° C. | 50 sec |
| Hold | 10° C. | Hold |

The amplified target biomarkers were then end-repaired in a reaction as follows.

| Reagent | Volume |
|---|---|
| PCR products from each reaction | 5 ul + 5 ul |
| T4 ligation Buffer | 10 ul |
| 10 mg/ml BSA | 1 ul |
| 10 mM dNTPs | 2 ul |
| T4 polymerase | 1 ul |
| T4 PNK | 1 ul |
| Nuclease-free Water | 75 ul |
| Total | 100 ul |

The mixture of the end-repair reaction was incubated at room temperature for 20 minutes. The DNA products were then purified using magnetic beads. Specifically, 150 μL of Agencourt® AMPure® XP Reagent (1.5× sample volume) was added to the sheared DNA sample, and thoroughly mixed with the bead suspension followed by incubation at room temperature for 5 minutes. The tube was then placed in a magnetic rack such as the DynaMag™-2 magnet for 3 minutes or until the solution was clear of brown tint when viewed at an angle. The supernatant was removed without disturbing the bead pellet. Without removing the tube from the magnet, the beads were washed twice with 500 μL of freshly prepared 70% ethanol. After the beads were dried, DNA was eluted with 42 μL of Nuclease-free water. An adaptor ligation reaction was then carried out by mixing 40 ul supernatant containing the eluted DNA with 5 ul ligation buffer, 1 ul Barcode X, 1 ul P1 adaptor, 1 ul 10 mM dNTPs, 1 ul of T4 ligase, and 1 ul Taq polymerase. The reaction mixture was placed on a thermocycler in a program of 22° C. 20 min, 72° C. 10 min. hold on 10° C. The reaction products were then purified with magnetic beads. The library was then amplified by adding a PCR mix (25 ul 2× Phusion HF PCR Master Mix, 1 ul Library Amplification Primers and 24 ul nuclease-free water) to the air-dry bead with the adaptor-ligated DNA products and incubating the mixture at room temperature for 2 minutes. The supernatant was then removed into a new tube and placed on a thermocycler to run the following program.

| Stage | Temperature | time |
|---|---|---|
| Hold. | 98° C. | 2 min |
| 8 cycles | 98° C. | 15 sec |
|  | 60° C. | 1 min |
| Hold | 10° C. | Hold |

The amplified library DNA was then purified with beads and quantified with Qubit assay with a Qubit 3.0 fluorometer according to the manufacturer's manual. The library DNA was then diluted to 15 ng/ml for template preparation The diluted library, an Ion 520 chip, consumables and reagents were loaded into Ion Chef instrument to perform emulsion PCR and enrich Ion sphere particles according to the manufacturer's standard instruction. Then put the prepared chip into the Ion S5 sequencer to start sequencing run. The mutation frequency of the three ctDNA tests are listed Table 5 below.

First, we applied CSMT-tools of tumor purity estimating modules to calculate the tumor cells percentage in tumor tissue. As the below figure shown the number is 54.1%. Second, we calculated the mutated clonal ratio for per somatic mutation in the Table 5. Last, based on ratio for each cell-free tumor somatic mutation DNA fragment in total cell free DNA and applied weighted average method (clonal ratio CR score is the weighted) to monitor the tumor load for this patient in three separate time point. Results were shown in FIG. 7.

TABLE 5

Mutation Frequency from the three DNA samples.

| Gene Name | Type | chromosome | Position | Reference | Alteration | somatic mutation clonal ratio | Frequency (%) First ctDNA | Second ctDNA | Third ctDNA |
|---|---|---|---|---|---|---|---|---|---|
| APC | stop_gained | 5 | 112175198 | C | T | 68.31% | 0.08 | 6 | 0.16 |
| BACE1 | sequence_feature | 11 | 117170531 | C | A | 16.95% | 0.01 | NA | 0.01 |
| BMP4 | synonymous_variant | 14 | 54418878 | C | T | 81.58% | 0.04 | 4.4 | 0.14 |
| CASKIN2 | sequence_feature | 17 | 73497828 | G | C | 43.39% | 0.01 | NA | 0.2 |
| CDH18 | missense_variant | 5 | 19721557 | A | T | 42.37% | 0.08 | 3.4 | 0.12 |
| CHD5 | sequence_feature | 1 | 6196771 | C | T | 70.68% | 0.05 | 4.6 | 0.17 |
| FGF18 | missense_variant | 5 | 170863239 | G | A | 44.75% | 0.09 | 3.1 | 0.14 |
| FLT4 | synonymous_variant | 5 | 180057043 | G | A | 64.24% | 0.11 | 6.6 | 0.25 |
| KIF17 | missense_variant | 1 | 21036291 | C | T | 59.83% | 0.05 | 3.7 | 0.06 |
| SESN3 | missense_variant | 11 | 94906470 | C | T | 18.81% | 0.08 | 6.1 | 0.52 |
| SLC35G3 | missense_variant | 17 | 33521058 | C | T | 53.81% | 0.05 | 4 | 0.2 |
| TP53 | stop_gained | 17 | 7577058 | C | A | 96.37% | 0.02 | 6.6 | 0.01 |
| TPP1 | splice_acceptor_variant&intron_variant | 11 | 6638091 | C | A | 55.85% | 0.08 | 6.7 | 0.2 |
| UQCRC2 | missense_variant | 16 | 21974100 | C | G | 43.78% | 0.06 | 4 | 0.36 |
| VWCE | missense_variant | 11 | 61048599 | C | A | 16.95% | 0.01 | NA | 0.01 |
| VWDE | missense_variant | 7 | 12409586 | G | T | 21.64% | 0.1 | 6.4 | 0.22 |

Figure 7:
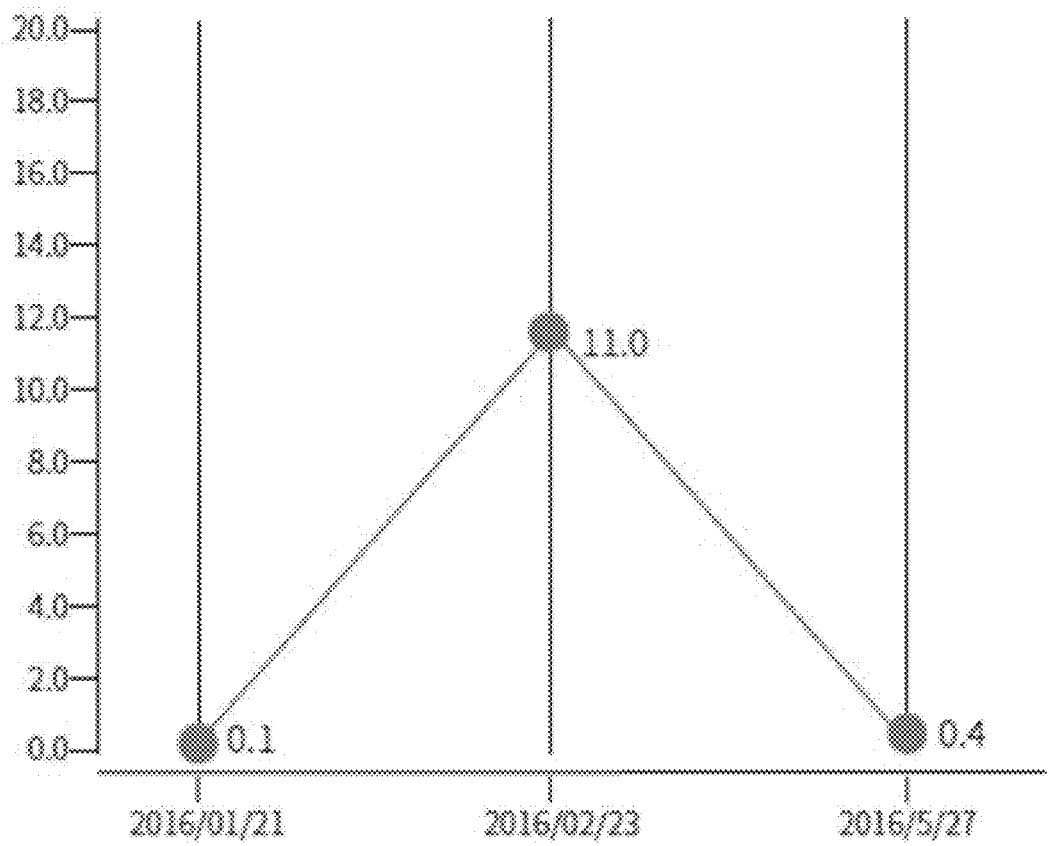
FIG. 7 shows a graph depicting the tumor load based in circulating tumor DNA in three samples obtained at three time points from a patient.
Figure 8A:
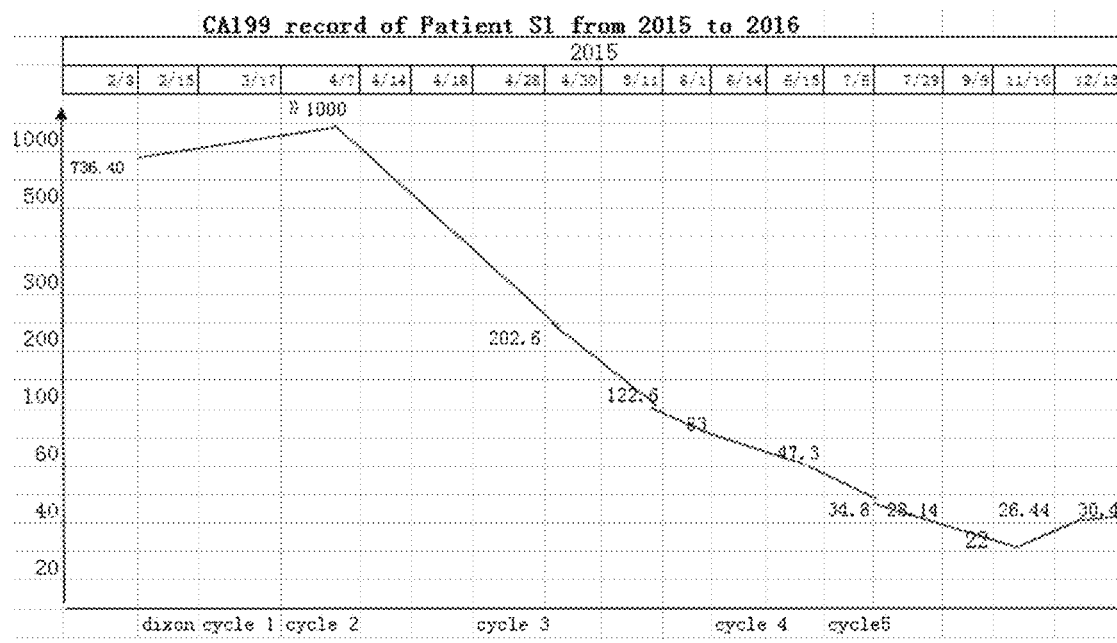
FIGS. 8A and 8B show graphs depicting the amount of CA199 tumor marker during the treatment of a tumor patient time-wisely from Feb. 3, 2015 to May 26, 2016. Past treatments: February 2015 Radical colon cancer resection; Mar. 18, 2015 Oxaliplatin200 mgd1+capecitabine1500 mg bid d1-14/q3w; Apr. 8, 2015 Oxaliplatin200 mgd1+capecitabine1500 mg bid d1-14+Bevacizumab d1/q3w; Apr. 29, 2015 Oxaliplatin200 mgd1+capecitabine1500 mg bid d1-14+Bevacizumab d1/q3w; Jun. 14, 2015 capecitabine1500 mg bid d1-14+Bevacizumab d1/q3w; Jul. 8, 2015 capecitabine1500 mg bid d1-14+Chinese Medicine/q3w; Jan. 20-Feb. 20, 2016 Crizotinib capsules 250 mg twice/day Mar. 8, 2016TACE; and Apr. 19, 2016 TACE.
Figure 8B:
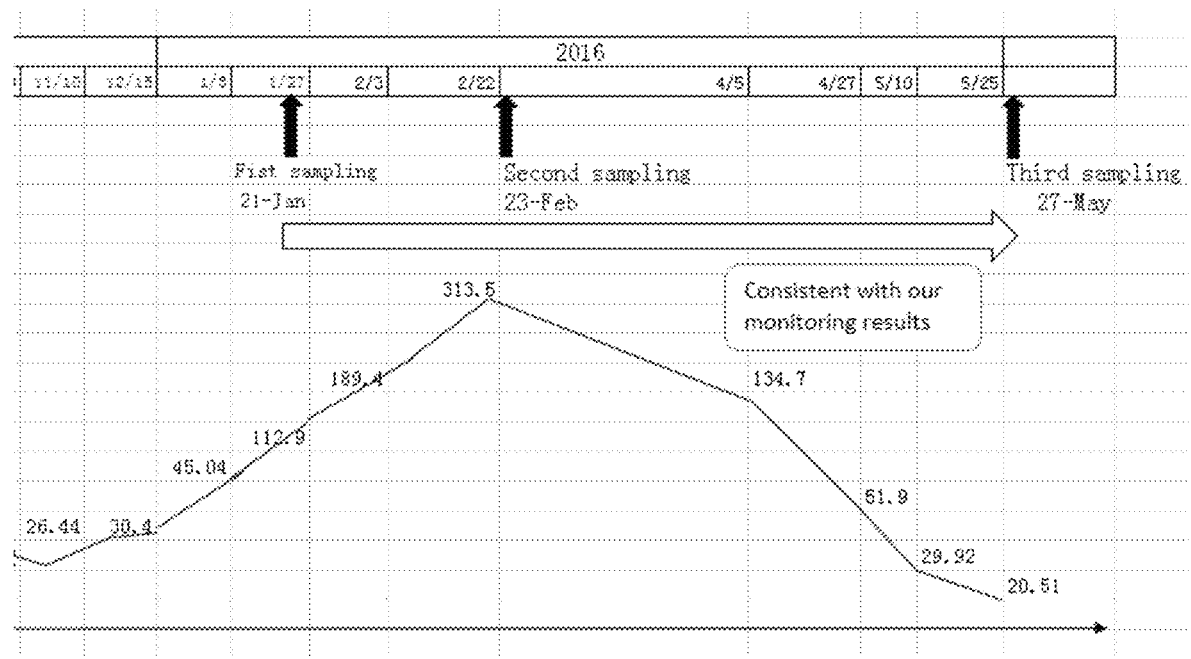

In this example, we obtained three blood samples from Patient S1 and performed the tests with both the customized and medicine pools. The input DNA is 2.3 ng, 3.68 ng and 4.3 ng, respectively. As shown in FIG. 7. The monitoring results showing the ratio of ctDNA in peripheral blood increased significantly from 0.1 in January 2016 to 11.0 in February 2016, then declined significantly from 11.0 in February 2016 to 0.4 in May 2016. As shown in FIGS. 8A and 8B, this fluctuation correlated with the patient's variation tendency of tumor marker CA199.

The sequencing results from the medicine pool with the second sampling showed a Panitunmumab tolerant mutation of KRAS. G13D and an Everolimus sensitive mutation of PIK3CA E545K. The detection of these drug sensitive mutations guided the upcoming treatment plans for the patient. The patient would then be treated with Panitumumab and/or Everolimus. See Table 6 below for the mutations.

TABLE 6

Mutations found with the medicine pool.

| chrom | Position | Ref | Variant | Type | Frequency | Gene | Mutation information |
|---|---|---|---|---|---|---|---|
| chr3 | 178936092 | A | C | SNP | 5.7 | PIK3CA | E545K |
| chr12 | 25398282 | C | T | SNP | 5.3 | KRAS | G13D |
| chr7 | 55241729 | — | T | INS | 8.5 | EGFR | |

We claim:

1. A method for monitoring tumor load in a patient, comprising:
   a. selecting a predetermined number of biomarker genes from DNA extracted from a tumor tissue sample from the patient to form a panel of biomarker genes;
   b. isolating circulating cell-free DNA fragments from a bodily fluid sample of the patient;
   c. enriching DNA sequences containing the biomarker genes in the cell-free DNA fragments;
   d. sequencing the enriched DNA sequences;
   e. counting the number of mutated DNA and normal DNA sequencing reads in the enriched DNA sequences; and
   f. obtaining a tumor load of the patient.

2. The method of claim 1, wherein the panel of biomarker gene includes at least 5 biomarker genes.

3. The method of claim 1, wherein the panel of biomarker genes includes 5-10 biomarker genes.

4. The method of claim 1, wherein the panel of biomarker genes includes 11-20 biomarker genes.

5. The method of claim 1 wherein the panel of biomarker genes includes 21-30 biomarker genes.

6. The method of claim 1, wherein the step c comprises the steps of:
   a. performing a multiplex PCR with primers specific to the biomarker genes in the panel of biomarker genes; and
   b. adding adaptors to the amplified DNA to obtain a library.

7. The method of claim 1, wherein the step d sequencing is performed on a Next Generation Sequencing platform.

8. The method of claim 1, further comprising: based on the obtained cell-free tumor load of the patient, guiding a treatment option for the patient.

9. The method of claim 1, further comprising repeating steps b-f in a periodic manner.

10. The method of claim 1, wherein the steps of b-f are repeated once every 1-3 months.

11. The method of claim 1, wherein selecting a predetermined number of biomarker genes comprises:
   a. determining somatic mutations in the DNA extracted from the tumor tissue sample of the patient;
   b. calculating a somatic mutation clonal ratio (CR) for each somatic mutation;
   c. ranking the somatic mutation clonal ratios for all somatic mutations; and
   d. selecting a predetermined number of somatic mutations as biomarker genes with mutation clonal ratios that are ranked the highest.

12. The method of claim 11, wherein calculating the somatic mutation clonal ratio (CR) comprises:
   a. determining the Tumor Purity (TP) which is defined as the percentage of tumor cells in the tumor tissue;
   b. determining, for each somatic mutation, somatic mutation allele ratio (SA);
   c. determining, for each somatic mutation, an average of the scores or values of a predetermining number of true germline heterozygosis SNPs in normal tissue nearest linked to the position of the somatic mutation (PLG);
   d. determining, for each somatic mutation, copy number variation (CNVR); and
   e. calculating the somatic mutation clonal ratio by $CR = SA/(PLG-((1-TP)/CNVR)*0.5)$.

13. The method of claim 1, wherein the step of obtaining a tumor load of the patient comprises:
   a. for each biomarker gene in the panel obtaining a somatic mutation allele ratio in circulating tumor DNA test by
      i. counting the number of total circulating DNA reads;
      ii. counting the number of circulating DNA with the somatic mutation allele reads; and
      iii. dividing the number of circulating DNA with the somatic mutation allele reads by the number of total circulating DNA reads to obtain the somatic mutation allele ratio;
   b. for each biomarker gene in the panel, obtaining a somatic mutation clonal ratio (CR) by:
      i. determining TP of the tumor tissue;
      ii. determining the SA for each somatic mutation;
      iii. determining the PLG for each somatic mutation;
      iv. determining the CNVR for each somatic mutation; and
      v. calculating the somatic mutation clonal ratio by $CR = SA/(PLG-((1-TP)/CNVR)*0.5)$; and
   c. obtaining the tumor load based on an average of the ratio of each somatic mutation allele ratio over the corresponding somatic mutation clonal ratio.

14. The method of claim 12, wherein determining the percentage of tumor cells in the tumor tissue (Tumor Purity) comprises:
   a. selecting true germline heterozygosis SNPs (THS) from the common SNPs in normal tissue;
   b. detecting the THS in the tumor tissue;
   c. plotting a density vs. THS allele ratio; and
   d. calculating the percentage of tumor cells in the tumor tissue based on the detected THS in the tumor tissue.

15. The method of claim 14, wherein detecting THS in the tumor tissue comprises:
   a. calling each THS allele score in the tumor tissue;
   b. using an algorithm to smooth score sets density curve;
   c. identifying the positions of two minor shoulder peaks on the density vs. THS allele ratio of the tumor tissue; and
   d. determining the percentage of tumor cell in the tumor tissue by $TP = ((100-(A+B))/2+A)/100$, where A is the position of a first of the minor shoulder peaks identified, and the B is the position of a second of the minor shoulder peaks identified.

16. The method of claim 1 further comprising detecting mutations in medicine genes, defined as genes related to therapeutic treatments.

17. The method of claim 16, wherein the detection of mutations in genes related to therapeutic treatments comprises:
   a. enriching DNA sequences containing the medicine genes in the cell-free circulating DNA;
   b. sequencing the enriched DNA; and c. counting the number of mutated DNA and the number of enriched DNA sequences.

18. The method of claim 17, wherein the enriching, sequencing and counting steps in the detection of mutations in medicine genes are performed simultaneously with the enriching, sequencing and counting steps in obtaining the tumor load based on the customized genes the panel of biomarker genes.

19. The method of claim 16, wherein the medicine genes comprise one or more genes selected from the group consisting of ERBB2, MET, EGFR, KRAS, PIK3CA, BRAF, KIT, NRAS, ALK, ROSI, and RET.

20. The method of claim 16, wherein the medicine genes comprise ERBB2, MET, EGFR, KRAS, PIK3CA, BRAF, KIT, NRAS, ALK, ROSI, and RET.

* * * * *

SEQUENCE LISTING

<160> NUMBER OF SEQ ID NOS: 68

<210> SEQ ID NO 1
<211> LENGTH: 27
<212> TYPE: DNA
<213> ORGANISM: Artificial Sequence
<220> FEATURE:
<223> OTHER INFORMATION: Oligo primer

<400> SEQUENCE: 1
taaaagtgaa tctgaggcat aactgca                27

<210> SEQ ID NO 2
<211> LENGTH: 22
<212> TYPE: DNA
<213> ORGANISM: Artificial Sequence
<220> FEATURE:
<223> OTHER INFORMATION: Oligo primer

<400> SEQUENCE: 2
cgcacagagg aagagaatct cc            22

<210> SEQ ID NO 3
<211> LENGTH: 29
<212> TYPE: DNA
<213> ORGANISM: Artificial Sequence
<220> FEATURE:
<223> OTHER INFORMATION: Oligo primer

<400> SEQUENCE: 3
agttcattat catctttgtc atcagctga           29

<210> SEQ ID NO 4
<211> LENGTH: 23
<212> TYPE: DNA
<213> ORGANISM: Artificial Sequence
<220> FEATURE:
<223> OTHER INFORMATION: Oligo primer

<400> SEQUENCE: 4
tcacaggatc ttcagctgac cta            23

<210> SEQ ID NO 5
<211> LENGTH: 19
<212> TYPE: DNA
<213> ORGANISM: Artificial Sequence
<220> FEATURE:
<223> OTHER INFORMATION: Oligo primer

<400> SEQUENCE: 5
ggtctcgcac tgcaggtac             19

<210> SEQ ID NO 6
<211> LENGTH: 20
<212> TYPE: DNA
<213> ORGANISM: Artificial Sequence
<220> FEATURE:
<223> OTHER INFORMATION: Oligo primer

<400> SEQUENCE: 6
caatgatggt ggccttgtcc            20

<210> SEQ ID NO 7
<211> LENGTH: 22
<212> TYPE: DNA
<213> ORGANISM: Artificial Sequence
<220> FEATURE:
<223> OTHER INFORMATION: Oligo primer

<400> SEQUENCE: 7
ccctgaatct cggcgacttt tt            22

<210> SEQ ID NO 8
<211> LENGTH: 22
<212> TYPE: DNA
<213> ORGANISM: Artificial Sequence
<220> FEATURE:
<223> OTHER INFORMATION: Oligo primer

<400> SEQUENCE: 8
cccagagaca ccatgattcc tg            22

<210> SEQ ID NO 9
<211> LENGTH: 22
<212> TYPE: DNA

```
<213> ORGANISM: Artificial Sequence
<220> FEATURE:
<223> OTHER INFORMATION: Oligo primer

<400> SEQUENCE: 9
ctacagccgg accagtggga aa                                                  22

<210> SEQ ID NO 10
<211> LENGTH: 22
<212> TYPE: DNA
<213> ORGANISM: Artificial Sequence
<220> FEATURE:
<223> OTHER INFORMATION: Oligo primer

<400> SEQUENCE: 10
gaaggacatg tacacgggta ca                                                  22

<210> SEQ ID NO 11
<211> LENGTH: 29
<212> TYPE: DNA
<213> ORGANISM: Artificial Sequence
<220> FEATURE:
<223> OTHER INFORMATION: Oligo primer

<400> SEQUENCE: 11
ctcaaatgtt ggctttacat ttttgactc                                           29

<210> SEQ ID NO 12
<211> LENGTH: 22
<212> TYPE: DNA
<213> ORGANISM: Artificial Sequence
<220> FEATURE:
<223> OTHER INFORMATION: Oligo primer

<400> SEQUENCE: 12
tgaggctgaa ggtcagctac tt                                                  22

<210> SEQ ID NO 13
<211> LENGTH: 20
<212> TYPE: DNA
<213> ORGANISM: Artificial Sequence
<220> FEATURE:
<223> OTHER INFORMATION: Oligo primer

<400> SEQUENCE: 13
cgaagaggcg catgaactga                                                     20

<210> SEQ ID NO 14
<211> LENGTH: 24
<212> TYPE: DNA
<213> ORGANISM: Artificial Sequence
<220> FEATURE:
<223> OTHER INFORMATION: Oligo primer

<400> SEQUENCE: 14
cccacagtgt cctcaattcc ttac                                                24

<210> SEQ ID NO 15
<211> LENGTH: 20
<212> TYPE: DNA
<213> ORGANISM: Artificial Sequence
<220> FEATURE:
<223> OTHER INFORMATION: Oligo primer

<400> SEQUENCE: 15
ggaggatgtg ggtagtcgtg                                                     20
```

```
<210> SEQ ID NO 16
<211> LENGTH: 23
<212> TYPE: DNA
<213> ORGANISM: Artificial Sequence
<220> FEATURE:
<223> OTHER INFORMATION: Oligo primer

<400> SEQUENCE: 16
agatgcttct gttgcttcct gag                                              23

<210> SEQ ID NO 17
<211> LENGTH: 31
<212> TYPE: DNA
<213> ORGANISM: Artificial Sequence
<220> FEATURE:
<223> OTHER INFORMATION: Oligo primer

<400> SEQUENCE: 17
atcaatcttg tagctgttta agaccctaaa a                                     31

<210> SEQ ID NO 18
<211> LENGTH: 23
<212> TYPE: DNA
<213> ORGANISM: Artificial Sequence
<220> FEATURE:
<223> OTHER INFORMATION: Oligo primer

<400> SEQUENCE: 18
aagaacaacc agtccaaggt agg                                              23

<210> SEQ ID NO 19
<211> LENGTH: 20
<212> TYPE: DNA
<213> ORGANISM: Artificial Sequence
<220> FEATURE:
<223> OTHER INFORMATION: Oligo primer

<400> SEQUENCE: 19
gttcatcagc gtgtagccga                                                  20

<210> SEQ ID NO 20
<211> LENGTH: 22
<212> TYPE: DNA
<213> ORGANISM: Artificial Sequence
<220> FEATURE:
<223> OTHER INFORMATION: Oligo primer

<400> SEQUENCE: 20
ctcagctgaa ggagcaccca ga                                               22

<210> SEQ ID NO 21
<211> LENGTH: 23
<212> TYPE: DNA
<213> ORGANISM: Artificial Sequence
<220> FEATURE:
<223> OTHER INFORMATION: Oligo primer

<400> SEQUENCE: 21
gctgtttcca taggtagggt cat                                              23

<210> SEQ ID NO 22
<211> LENGTH: 30
<212> TYPE: DNA
<213> ORGANISM: Artificial Sequence
<220> FEATURE:
```

```
<223> OTHER INFORMATION: Oligo primer

<400> SEQUENCE: 22
cagcataccc attttctgtg ttcaaattaa                                      30

<210> SEQ ID NO 23
<211> LENGTH: 22
<212> TYPE: DNA
<213> ORGANISM: Artificial Sequence
<220> FEATURE:
<223> OTHER INFORMATION: Oligo primer

<400> SEQUENCE: 23
tgacagaggg tcaaggtgct at                                              22

<210> SEQ ID NO 24
<211> LENGTH: 22
<212> TYPE: DNA
<213> ORGANISM: Artificial Sequence
<220> FEATURE:
<223> OTHER INFORMATION: Oligo primer

<400> SEQUENCE: 24
cagccaaacg gatctggaag aa                                              22

<210> SEQ ID NO 25
<211> LENGTH: 19
<212> TYPE: DNA
<213> ORGANISM: Artificial Sequence
<220> FEATURE:
<223> OTHER INFORMATION: Oligo primer

<400> SEQUENCE: 25
tgctgccgta gaagtcagg                                                  19

<210> SEQ ID NO 26
<211> LENGTH: 19
<212> TYPE: DNA
<213> ORGANISM: Artificial Sequence
<220> FEATURE:
<223> OTHER INFORMATION: Oligo primer

<400> SEQUENCE: 26
ggcatcaagt gcccttcct                                                  19

<210> SEQ ID NO 27
<211> LENGTH: 22
<212> TYPE: DNA
<213> ORGANISM: Artificial Sequence
<220> FEATURE:
<223> OTHER INFORMATION: Oligo primer

<400> SEQUENCE: 27
catgtactgg tccctcattg ca                                              22

<210> SEQ ID NO 28
<211> LENGTH: 23
<212> TYPE: DNA
<213> ORGANISM: Artificial Sequence
<220> FEATURE:
<223> OTHER INFORMATION: Oligo primer

<400> SEQUENCE: 28
caggaacgta ctggtgaaaa cac                                             23
```

-continued

```
<210> SEQ ID NO 29
<211> LENGTH: 19
<212> TYPE: DNA
<213> ORGANISM: Artificial Sequence
<220> FEATURE:
<223> OTHER INFORMATION: Oligo primer

<400> SEQUENCE: 29
gccagggtat gtggctaca                                              19

<210> SEQ ID NO 30
<211> LENGTH: 29
<212> TYPE: DNA
<213> ORGANISM: Artificial Sequence
<220> FEATURE:
<223> OTHER INFORMATION: Oligo primer

<400> SEQUENCE: 30
tcagtggaaa aatagcctca attcttacc                                   29

<210> SEQ ID NO 31
<211> LENGTH: 19
<212> TYPE: DNA
<213> ORGANISM: Artificial Sequence
<220> FEATURE:
<223> OTHER INFORMATION: Oligo primer

<400> SEQUENCE: 31
gaagcctacg tgatggcca                                              19

<210> SEQ ID NO 32
<211> LENGTH: 28
<212> TYPE: DNA
<213> ORGANISM: Artificial Sequence
<220> FEATURE:
<223> OTHER INFORMATION: Oligo primer

<400> SEQUENCE: 32
gtgggatcat attcatctac aaagtggt                                    28

<210> SEQ ID NO 33
<211> LENGTH: 22
<212> TYPE: DNA
<213> ORGANISM: Artificial Sequence
<220> FEATURE:
<223> OTHER INFORMATION: Oligo primer

<400> SEQUENCE: 33
gcctcttaca cccagtggag aa                                          22

<210> SEQ ID NO 34
<211> LENGTH: 23
<212> TYPE: DNA
<213> ORGANISM: Artificial Sequence
<220> FEATURE:
<223> OTHER INFORMATION: Oligo primer

<400> SEQUENCE: 34
ggcacggttg aatgtaaggc tta                                         23

<210> SEQ ID NO 35
<211> LENGTH: 24
<212> TYPE: DNA
<213> ORGANISM: Artificial Sequence
<220> FEATURE:
<223> OTHER INFORMATION: Oligo primer
```

<400> SEQUENCE: 35
cccacagaaa cccatgtatg aagt                                          24

<210> SEQ ID NO 36
<211> LENGTH: 21
<212> TYPE: DNA
<213> ORGANISM: Artificial Sequence
<220> FEATURE:
<223> OTHER INFORMATION: Oligo primer

<400> SEQUENCE: 36
ctcccatacc ctctcagcgt a                                             21

<210> SEQ ID NO 37
<211> LENGTH: 30
<212> TYPE: DNA
<213> ORGANISM: Artificial Sequence
<220> FEATURE:
<223> OTHER INFORMATION: Oligo primer

<400> SEQUENCE: 37
aatcttttga tgacattgca tacattcgaa                                    30

<210> SEQ ID NO 38
<211> LENGTH: 23
<212> TYPE: DNA
<213> ORGANISM: Artificial Sequence
<220> FEATURE:
<223> OTHER INFORMATION: Oligo primer

<400> SEQUENCE: 38
gccagttaac gtcttccttc tct                                           23

<210> SEQ ID NO 39
<211> LENGTH: 30
<212> TYPE: DNA
<213> ORGANISM: Artificial Sequence
<220> FEATURE:
<223> OTHER INFORMATION: Oligo primer

<400> SEQUENCE: 39
tacagagtaa cagactagct agagacaatg                                    30

<210> SEQ ID NO 40
<211> LENGTH: 20
<212> TYPE: DNA
<213> ORGANISM: Artificial Sequence
<220> FEATURE:
<223> OTHER INFORMATION: Oligo primer

<400> SEQUENCE: 40
gtgtgcaccg gcacagacat                                               20

<210> SEQ ID NO 41
<211> LENGTH: 29
<212> TYPE: DNA
<213> ORGANISM: Artificial Sequence
<220> FEATURE:
<223> OTHER INFORMATION: Oligo primer

<400> SEQUENCE: 41
tacctctatt gttggatcat attcgtcca                                     29

<210> SEQ ID NO 42
<211> LENGTH: 23

```
<212> TYPE: DNA
<213> ORGANISM: Artificial Sequence
<220> FEATURE:
<223> OTHER INFORMATION: Oligo primer

<400> SEQUENCE: 42
cagtcaaggt tgctgatttt ggt                                          23

<210> SEQ ID NO 43
<211> LENGTH: 29
<212> TYPE: DNA
<213> ORGANISM: Artificial Sequence
<220> FEATURE:
<223> OTHER INFORMATION: Oligo primer

<400> SEQUENCE: 43
tattatgact tgtcacaatg tcaccacat                                    29

<210> SEQ ID NO 44
<211> LENGTH: 26
<212> TYPE: DNA
<213> ORGANISM: Artificial Sequence
<220> FEATURE:
<223> OTHER INFORMATION: Oligo primer

<400> SEQUENCE: 44
gaggttaata tccgcaaatg acttgc                                       26

<210> SEQ ID NO 45
<211> LENGTH: 26
<212> TYPE: DNA
<213> ORGANISM: Artificial Sequence
<220> FEATURE:
<223> OTHER INFORMATION: Oligo primer

<400> SEQUENCE: 45
ctctgtttta agatctgggc agtgaa                                       26

<210> SEQ ID NO 46
<211> LENGTH: 22
<212> TYPE: DNA
<213> ORGANISM: Artificial Sequence
<220> FEATURE:
<223> OTHER INFORMATION: Oligo primer

<400> SEQUENCE: 46
acatttccag tcctgcagtc aa                                           22

<210> SEQ ID NO 47
<211> LENGTH: 26
<212> TYPE: DNA
<213> ORGANISM: Artificial Sequence
<220> FEATURE:
<223> OTHER INFORMATION: Oligo primer

<400> SEQUENCE: 47
tattcacaga gacttggcag ccagaa                                       26

<210> SEQ ID NO 48
<211> LENGTH: 28
<212> TYPE: DNA
<213> ORGANISM: Artificial Sequence
<220> FEATURE:
<223> OTHER INFORMATION: Oligo primer

<400> SEQUENCE: 48
```

```
gtaataatcc agactgtgtt tctcccttt                                          28

<210> SEQ ID NO 49
<211> LENGTH: 23
<212> TYPE: DNA
<213> ORGANISM: Artificial Sequence
<220> FEATURE:
<223> OTHER INFORMATION: Oligo primer

<400> SEQUENCE: 49
gaaaatgctg gctgacctaa agc                                                23

<210> SEQ ID NO 50
<211> LENGTH: 20
<212> TYPE: DNA
<213> ORGANISM: Artificial Sequence
<220> FEATURE:
<223> OTHER INFORMATION: Oligo primer

<400> SEQUENCE: 50
acttctcaca ccgctgtgtt                                                    20

<210> SEQ ID NO 51
<211> LENGTH: 30
<212> TYPE: DNA
<213> ORGANISM: Artificial Sequence
<220> FEATURE:
<223> OTHER INFORMATION: Oligo primer

<400> SEQUENCE: 51
cttcatgaag acctcacagt aaaaataggt                                         30

<210> SEQ ID NO 52
<211> LENGTH: 22
<212> TYPE: DNA
<213> ORGANISM: Artificial Sequence
<220> FEATURE:
<223> OTHER INFORMATION: Oligo primer

<400> SEQUENCE: 52
ttgtctttgt gttcccggac at                                                 22

<210> SEQ ID NO 53
<211> LENGTH: 26
<212> TYPE: DNA
<213> ORGANISM: Artificial Sequence
<220> FEATURE:
<223> OTHER INFORMATION: Oligo primer

<400> SEQUENCE: 53
gattactggt ttccaacagg ttcttg                                             26

<210> SEQ ID NO 54
<211> LENGTH: 23
<212> TYPE: DNA
<213> ORGANISM: Artificial Sequence
<220> FEATURE:
<223> OTHER INFORMATION: Oligo primer

<400> SEQUENCE: 54
tgtgccaggg accttacctt ata                                                23

<210> SEQ ID NO 55
<211> LENGTH: 28
<212> TYPE: DNA
<213> ORGANISM: Artificial Sequence
```

```
<220> FEATURE:
<223> OTHER INFORMATION: Oligo primer

<400> SEQUENCE: 55
actgatatgg tagacagagc ctaaacat                                    28

<210> SEQ ID NO 56
<211> LENGTH: 22
<212> TYPE: DNA
<213> ORGANISM: Artificial Sequence
<220> FEATURE:
<223> OTHER INFORMATION: Oligo primer

<400> SEQUENCE: 56
actgaccaaa actcagcctg tt                                          22

<210> SEQ ID NO 57
<211> LENGTH: 21
<212> TYPE: DNA
<213> ORGANISM: Artificial Sequence
<220> FEATURE:
<223> OTHER INFORMATION: Oligo primer

<400> SEQUENCE: 57
agccataggg cataagctgt g                                           21

<210> SEQ ID NO 58
<211> LENGTH: 28
<212> TYPE: DNA
<213> ORGANISM: Artificial Sequence
<220> FEATURE:
<223> OTHER INFORMATION: Oligo primer

<400> SEQUENCE: 58
gtggaagatc aatccattt ttgttgtc                                     28

<210> SEQ ID NO 59
<211> LENGTH: 25
<212> TYPE: DNA
<213> ORGANISM: Artificial Sequence
<220> FEATURE:
<223> OTHER INFORMATION: Oligo primer

<400> SEQUENCE: 59
aactcacatc gaggatttcc ttgtt                                       25

<210> SEQ ID NO 60
<211> LENGTH: 27
<212> TYPE: DNA
<213> ORGANISM: Artificial Sequence
<220> FEATURE:
<223> OTHER INFORMATION: Oligo primer

<400> SEQUENCE: 60
tagcacttac ctgtgactcc atagaaa                                     27

<210> SEQ ID NO 61
<211> LENGTH: 20
<212> TYPE: DNA
<213> ORGANISM: Artificial Sequence
<220> FEATURE:
<223> OTHER INFORMATION: Oligo primer

<400> SEQUENCE: 61
gtgggcaggt aggtgagttc                                             20
```

<210> SEQ ID NO 62
<211> LENGTH: 30
<212> TYPE: DNA
<213> ORGANISM: Artificial Sequence
<220> FEATURE:
<223> OTHER INFORMATION: Oligo primer

<400> SEQUENCE: 62
tattataagg cctgctgaaa atgactgaat                                30

<210> SEQ ID NO 63
<211> LENGTH: 26
<212> TYPE: DNA
<213> ORGANISM: Artificial Sequence
<220> FEATURE:
<223> OTHER INFORMATION: Oligo primer

<400> SEQUENCE: 63
cttggtggta aacttttgag tttgca                                    26

<210> SEQ ID NO 64
<211> LENGTH: 25
<212> TYPE: DNA
<213> ORGANISM: Artificial Sequence
<220> FEATURE:
<223> OTHER INFORMATION: Oligo primer

<400> SEQUENCE: 64
gactcgagtg atgattggga gattc                                     25

<210> SEQ ID NO 65
<211> LENGTH: 25
<212> TYPE: DNA
<213> ORGANISM: Artificial Sequence
<220> FEATURE:
<223> OTHER INFORMATION: Oligo primer

<400> SEQUENCE: 65
aaacctgttt gttggacata ctgga                                     25

<210> SEQ ID NO 66
<211> LENGTH: 29
<212> TYPE: DNA
<213> ORGANISM: Artificial Sequence
<220> FEATURE:
<223> OTHER INFORMATION: Oligo primer

<400> SEQUENCE: 66
gctcggtagt ctacagattc atttgaaac                                 29

<210> SEQ ID NO 67
<211> LENGTH: 24
<212> TYPE: DNA
<213> ORGANISM: Artificial Sequence
<220> FEATURE:
<223> OTHER INFORMATION: Oligo primer

<400> SEQUENCE: 67
cttgtagatt gcaggcagac agat                                      24

<210> SEQ ID NO 68
<211> LENGTH: 24
<212> TYPE: DNA
<213> ORGANISM: Artificial Sequence
<220> FEATURE:
<223> OTHER INFORMATION: Oligo primer

```
<400> SEQUENCE: 68
gcagagaatg ggtactcacg tttc                                              24
```